United States Patent
Tao

(10) Patent No.: US 11,635,431 B2
(45) Date of Patent: Apr. 25, 2023

(54) APPARATUS FOR ANALYZING AND DETECTING INTERACTIONS AND REACTIONS OF MOLECULES

(71) Applicant: ARIZONA BOARD OF REGENTS ON BEHALF OF ARIZONA STATE UNIVERSITY, Scottsdale, AZ (US)

(72) Inventor: Nongjian Tao, Fountain Hills, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 291 days.

(21) Appl. No.: 16/613,745

(22) PCT Filed: May 18, 2018

(86) PCT No.: PCT/US2018/033520
§ 371 (c)(1),
(2) Date: Nov. 14, 2019

(87) PCT Pub. No.: WO2018/213790
PCT Pub. Date: Nov. 22, 2018

(65) Prior Publication Data
US 2021/0172944 A1    Jun. 10, 2021

Related U.S. Application Data

(60) Provisional application No. 62/508,029, filed on May 18, 2017.

(51) Int. Cl.
*G01N 33/557* (2006.01)
*G01N 33/84* (2006.01)
(Continued)

(52) U.S. Cl.
CPC ......... *G01N 33/557* (2013.01); *C12Q 1/6825* (2013.01); *G01N 33/543* (2013.01);
(Continued)

(58) Field of Classification Search
CPC .. G01N 33/557; G01N 33/543; G01N 33/552; G01N 33/553; G01N 33/84;
(Continued)

(56) References Cited

U.S. PATENT DOCUMENTS

2002/0076717 A1 * 6/2002 Makino ............... C12Q 1/6825
435/6.11
2005/0003399 A1   1/2005 Blackburn
(Continued)

FOREIGN PATENT DOCUMENTS

WO   WO-2005108612 A2 * 11/2005  ........... C12Q 1/6825
WO   WO-2016012451 A1 *  1/2016  ............. C07K 14/47
WO   WO-2016160131 A1 * 10/2016  ........ B01L 3/502761

OTHER PUBLICATIONS

Fang et al., Real-time monitoring of phosphorylation kinetics with self-assembled nano-oscillators, Angew. Chem. Int. Ed. 2015, 54, 2538-2542 (Year: 2015).*
(Continued)

*Primary Examiner* — Samuel P Siefke
*Assistant Examiner* — Henry H Nguyen
(74) *Attorney, Agent, or Firm* — Quarles & Brady LLP

(57) ABSTRACT

An apparatus for label-free analysis of molecules, including interactions and reactions of the molecules, is disclosed. The apparatus is based on detecting molecule movement under the influence of an external electric field. The apparatus is able to achieve sensitive detection of molecular binding to proteins or other molecules, and conformational changes of proteins or other molecules and biochemical reactions of the proteins or other molecules. Applications of the apparatus include screening of drug molecules, kinetic analysis of posttranslational modification of proteins, and small molecule-protein interactions.

17 Claims, 2 Drawing Sheets

(51) Int. Cl.
  *G01N 33/552* (2006.01)
  *G01N 33/553* (2006.01)
  *G01N 33/543* (2006.01)
  *G01B 11/14* (2006.01)
  *G01N 21/17* (2006.01)
  *C12Q 1/6825* (2018.01)

(52) U.S. Cl.
  CPC ......... *G01N 33/552* (2013.01); *G01N 33/553* (2013.01); *G01N 33/84* (2013.01); *G01B 11/14* (2013.01); *G01N 2021/1721* (2013.01)

(58) Field of Classification Search
  CPC ................. G01B 11/14; C12Q 1/6825; C12Q 2563/116; C12Q 2565/519; C12Q 2565/607; C12Q 2565/628; C12Q 2565/601
  See application file for complete search history.

(56) References Cited

U.S. PATENT DOCUMENTS

| | | | |
|---|---|---|---|
| 2005/0048599 A1* | 3/2005 | Goldberg | B82Y 5/00 435/34 |
| 2005/0214789 A1* | 9/2005 | Moyle | C12Q 1/6841 435/6.12 |
| 2007/0181424 A1 | 8/2007 | Frey | |
| 2010/0009872 A1 | 1/2010 | Eid | |
| 2010/0256004 A1* | 10/2010 | Tashiro | C12Q 1/6837 506/9 |
| 2010/0294659 A1* | 11/2010 | Green | C12Q 1/6825 204/400 |
| 2011/0236984 A1* | 9/2011 | Sun | C12Q 1/6869 436/94 |
| 2012/0309651 A1* | 12/2012 | Pregibon | C12Q 1/6895 977/773 |

OTHER PUBLICATIONS

Fang, Y. et al. "Real-Time Monitoring of Phosphorylation Kinetics with Self-Assembled Nano-oscillators." Angewandte Chemie International Edition 54.8 (2015): 2538-2542.

International Searching Authority. International Search Report and Written Opinion for application PCT/US2018/033520, dated Aug. 10, 2018.

Shan, X. et al. "Detection of charges and molecules with self-assembled nano-oscillators." Nano letters 14.7 (2014): 4151-4157.

Vollmer, F. et al. "Whispering-gallery-mode biosensing: label-free detection down to single molecules." Nature methods 5.7 (2008): 591-596.

Zijlstra, P. et al. "Optical detection of single non-absorbing molecules using the surface plasmon resonance of a gold nanorod." Nature nanotechnology 7.6 (2012): 379-382.

* cited by examiner

APPARATUS FOR ANALYZING AND DETECTING INTERACTIONS AND REACTIONS OF MOLECULES

CROSS REFERENCE TO RELATED APPLICATIONS

This application is a U.S. National Stage of PCT Application No. PCT/US2018/033520 filed on May 18, 2018 which claims a priority benefit from, and incorporates herein by reference, U.S. Provisional Patent Application No. 62/508,029, filed May 18, 2017, and entitled "apparatus for analyzing and detecting interactions and reactions of molecules."

TECHNICAL FIELD

This disclosure relates to an apparatus for label-free analysis of molecules.

BACKGROUND

Detecting molecular biomarkers for disease diagnosis, discovering, screening and validating drugs, and performing molecular scale biomedical research all require measurement of interactions, reactions and conformational changes of molecules, such as proteins. The interactions include binding between molecules, and the reactions include post-translational modification of proteins. The currently available detection technologies fall into two categories, label-based and label-free technologies. The former uses a label (fluorescent dye molecules, quantum dots or radio-active isotopes). Labels can structurally and functionally interfere with an assay, may not be specific and may be difficult to conjugate—a problem often encountered in single-molecule experiments. Although specific, label-based approach is an end-point assay—detecting molecules before and after binding to another molecule only, which lacks kinetic information.

The label-free approach is particularly attractive for kinetic studies as it monitors the binding or reaction of processes in real time, but its sensitivity often diminishes with the size of the molecule, marking it hard to detect small molecules. The current label-free technologies are also difficult to detect conformational changes and biochemical reactions of molecules.

In addition to the analysis of molecular interactions, reactions, and conformational changes, detecting and identifying molecules based on the distinct mobility of each molecule are also important. Mobility here refers to movement of the molecule in response to an electric field, which is determined by the charge, mass and other physical properties of the molecule.

Another analytical method for the analysis molecules is to measure the isoelectric point, the pH of the solution at which the molecule is neural. When the solution pH is higher or lower than the isoelectric point, the molecule is charged due to protonation or deprotonation.

In both the mobility and isoelectric point measurements, the current methods are not compatible to the microarray platform, which prints molecules on a surface in arrays to allow high throughout analysis of the molecules.

SUMMARY

Embodiments of the present disclosure provide an apparatus for analyzing and detecting interactions and reactions of molecules. The apparatus comprises a surface configured to conduct electricity; a molecular bridge configured to bind to said surface and to bind to a molecule; at least one electrode configured to form an electric field between the electrode and the surface; and a solution, wherein the surface, the molecular bridge, and at least a portion of the electrode are submerged in the solution. Further, the apparatus comprises a sensor configured to measure the change in a distance between the molecule and the surface.

In certain embodiments, the conductive surface comprises a glass substrate coated with a metal film. In other embodiments, the conductive surface comprises a glass substrate coated with indium tin oxide, or graphene, or other thin carbon film.

Further, the apparatus in an embodiment contains a light emitting device, wherein the light emitting device is selected from the group consisting of a laser, a light emitting diode, and a superluminescent light emitting diode. In certain embodiments, the sensor is selected from the group consisting of a surface plasmon resonance (SPR) sensor, a total internal reflection microscope, and a transmitted optical microscope.

BRIEF DESCRIPTION OF DRAWINGS

The technology disclosed herein will be better understood from a reading of the following detailed description taken in conjunction with the drawings in which like reference designators are used to designate like elements, and in which.

DETAILED DESCRIPTION

The present disclosure overcomes the issues of decreased sensitivities in detecting small molecules and difficulties to detect conformational changes and biochemical reactions of molecules with the current label-free technologies. It further provides a way to identify molecules based on its mobility and isoelectric point in a micro-array compatible format.

This technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

Figure 1:
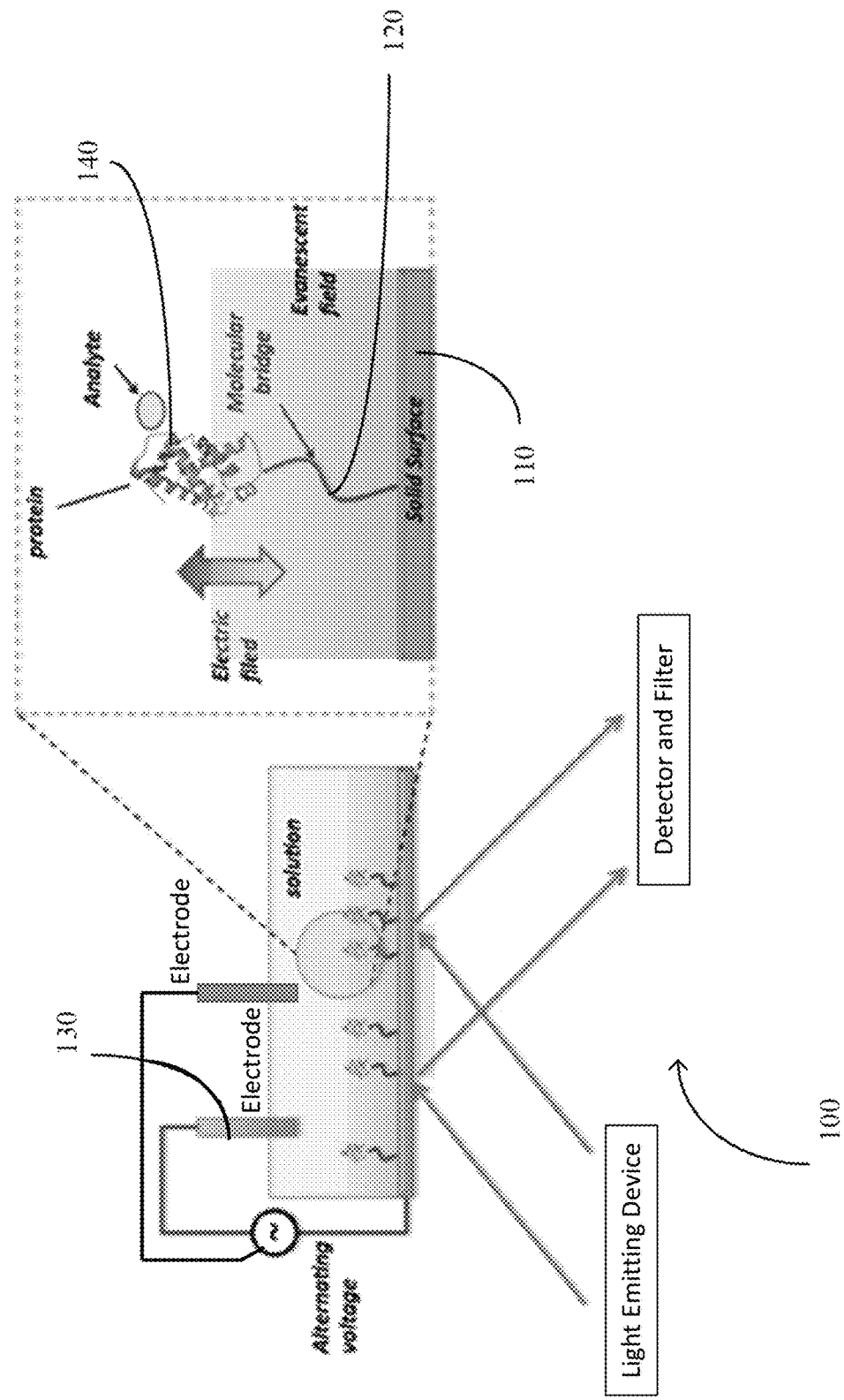
FIG. 1 illustrates one embodiment of an apparatus for analyzing and detecting molecules.

Referring to FIG. 1, an apparatus embodiment 100 comprises the following components: a surface 110, to which a biological object 140 is tethered via a molecule bridge 120, and an electrode 130. In certain embodiments, the surface 110, the molecule bridge 120, and the biological object 140 are submerged in a solution. Further, at least a portion of the electrode 130 is submerged in the solution so that when a voltage is applied, an electric filed is able to form between the surface 110 and the electrode 130. In some embodiments, the solution is a 1 mM acetate buffer with a pH of about (±1) 5.3. In other embodiments, the solution can be diluted phosphate buffer solution (PBS). It is known to a person skilled in the art that any solution that can conduct electricity can be used. Further, the pH value of the solution can be adjusted based on different applications of the apparatus 100 for various analysis of biological materials. In some embodiments, the biological object 140 may be a protein. In other embodiments, the biological object 140 may be a virus or other molecules expressed on the surface of the virus. In yet other embodiments, the biological object 140 may be a bacterial cell with proteins or other molecules expressed on the surface of the bacterial cell. In certain embodiments, the biological object 140 could have an analyte coupled to it. The analyte could be a protein, nucleic acid, peptide, drug, ion, or other molecules. The analyte can interact with the biological object 140 and change the mobility of the object 140.

In certain embodiments, the apparatus 100 is designed to analyze and detect the movement of the biological object 140 in response to the electric field. The movement of the biological object 140 reflects the properties of the object, such as, the size, surface hydrophobicity, charge and mass of the object 140. For example, after post translation, such as phosphorylation of a protein, the properties of the phosphorylated protein are changed. Therefore, the movement of the phosphorylated proteins in an electric field are different compared to unphosphorylated proteins.

Further, the apparatus 100 is able to gather information about the object, molecular binding, biochemical reactions, conformational changes, and mobility by detecting the movement of the object under the influence of the electric field. By change the pH of the solution, it further determines the isoelectric point of the molecule. Applications of the apparatus 100 for analysis of various biological materials, such as detecting post translational modifications of proteins, screening drug candidates, detecting molecules express on virus or bacterial cells, and studying protein conformational changes, will be discussed in more details below.

Referring back to FIG. 1, in certain embodiments, the molecular bridge 120 has a length of about 10 nm to about 999 nm. If the molecular bridge 120 is too short, for examples shorter than tens of nm, it may lead to strong interaction between the neighboring biological molecules. If the molecular bridge 120 is too long, for example longer than hundreds of nm, it may lead to increased unwanted Brownian motion that affects the detection of the movement of the biological object 140. In some embodiments, the molecule bridge 120 comprises an electrically neutral polymer. For example, the electrically neutral polymer may be polyethylene glycol (PEG) having a number average molar mass of about 1.6 kD to 160 kD. PEG is electrically neutral so that it does not respond to the electric field. Further, it does not interact with proteins and other biological molecules. In certain embodiments, the PEG contains a biotin group and an N-Hydroxysuccinimide (NHS) group on either end of PEG molecule bridge 120. The NHS group facilitates binding between one end of the PEG molecule bridge 120 to the biological object 140. And the biotin group facilitates binding between the other end of the PEG molecule bridge 120 to the surface 110. In other embodiments, the molecule bridge 120 comprises the deoxyribonucleic acid (DNA) sequence. A DNA sequence is charged, however, it is easy to synthesize the molecule bridge 120 comprising a DNA molecule with different sequences and length.

With respect to the surface 110, in some embodiment, the surface 110 comprises a glass substrate coated with a metal film. The metal may be gold and the metal film may have a thickness of about 47 nm. In other embodiments, the surface 110 comprises a glass substrate coated with indium tin oxide (ITO). In yet other embodiments, the surface 110 comprises a glass substrate coated with graphene. ITO is a ternary composition of indium, tin and oxygen in varying proportions. ITO is a transparent conducting oxides. Graphene, a thin layer of pure carbon, is another material that has electrical conductivity and optical transparency. In yet other embodiments, the surface 110 comprises a glass substrate coated with a thin carbon film. These conductive materials make it easy to apply the electric field, and also allows surface plasmon resonance detection of the movement of the object, which will be described below. In certain embodiments, the surface 110 also comprises streptavidin or other molecules that allows binding to one end of the molecule bridge 120.

Now referring to the electric field, the electrode 130 is disposed in a way that when a voltage is applied, the electric field formed has a direction that is substantially orthogonal to the surface 110. In some embodiments, a periodic alternating current (AC) at a frequency is used to generate the electric field so that the biological object moves up and down periodically and the movement of the biological subject is detected using a filter to selectively detect the response at the frequency of the applied alternating voltage. The applied voltage is preferred to be less than 10 volts in order to minimize unwanted electrochemical reactions taking place on the solid surface and the electrode. In certain embodiments, the frequency has a range of 0.1 Hz to 10 kilo-Hz. Lower frequencies lead to slow overall detection time, and high frequencies make the system hard to follow. In certain embodiments, the standard three-electrode electrochemical may be used, which the surface is used as a working electrode, the apparatus 100 further comprises a reference electrode, and the electrode 130 is used as a counter electrode. Both the reference electrode and the counter electrode are inserted in the solution.

With respect to detecting the movement of the biological object, a surface plasmon resonance (SPR) detection or imaging technique is utilized. In this embodiment, a metal film with an appropriate thickness (about 47 nm gold) is coated on a glass surface. Light from a laser, or light emitting diode, or a superluminescent light emitting diode, is directed to the metal film with an appropriate incident angle to excite surface plasmons in the metal film. Associated with the surface plasmon excitation is an evanescent electromagnetic wave with amplitude decays exponentially from the surface of the metal film into the solution, and diminishes over a few hundred nm. When the biological object 140 is close to the metal film, it interacts with the evanescent electromagnetic wave and cause a change in the surface plasmons. When the biological object 140 moves away from the surface, where the evanescent electromagnetic wave is weak, it causes a less change in the surface plasmons. By detecting the surface plasmons with a camera or photodetector, a person with ordinary skill in the art can measure the movement of the biological object 140 in response to the applied voltage sensitively. Fang et al., Real-time monitoring of phosphorylation kinetics with self-assembled nano-oscillators, Angew. Chem. Int. Ed. 2015, 54, 2538-2542 is incorporated herein.

In other embodiments, the surface 110 is a glass substrate coated with transparent and conductive materials. Light from a laser, or light emitting diode, or a superluminescent light emitting diode, is directed to the transparent material at an incident angle, greater or equal to the critical angle, such that a total internal reflection condition is reach. An evanescent electromagnetic wave with amplitude decays exponentially from the surface of the transparent material surface into the solution, and diminishes over a few hundred nm. When the biological object 140 is close to the surface, it interacts with the evanescent electromagnetic wave and cause scattering of light. When the biological object 140 moves away from the surface, where the evanescent electromagnetic wave is weak, it causes a less scattering of light. By detecting light scattering with a camera or photodetector, one can measure the movement of the object in response to the applied voltage sensitively.

Applications of the Present Embodiments

Detecting Post Translation Modifications of Proteins

Post translation modifications of proteins are critically important in diseases initiation and progression (e.g., cancer). A particularly important example is phosphorylation, which is a biochemical reaction, involving the addition of a phosphate group to a protein with the help enzymes. Protein phosphorylation plays a significant role in a wide range of cellular processes, and has been the subject of a very large body of research. Detection of phosphorylation, particularly quantification of phosphorylation kinetics, has been a difficult task using the current detection technologies because the phosphate is small. The present apparatus is ideal for detecting phosphorylation and dephosphorylation, and quantifying the kinetics, because the processes are associated with charge changes, which will affect the movement of the protein under the applied voltage.

Screening Drug Candidates

A unique advantage of the present apparatus is the ability to quantify the binding kinetics not only small large molecules but also small molecules that are difficult with the existing detection technologies. Detecting small molecules are important because most drug molecules are small molecules. When a small molecule binds to a protein tethered to the surface, it modifies the properties of the protein (charge, conformation, or surface hydrophobicity etc.), which is reflected in the movement of the protein.

Detecting Molecules Express on Virus or Bacterial Cells

The biological object can be a virus or bacterial cell tethered on the surface. One attractive application is to study membrane proteins and their binding prosperities to different molecules. Membrane proteins on cell surfaces serve as communication gateways for various cellular signaling processes, and are preferred targets for drugs. In fact, over 60% drugs target membrane proteins. Despite the importance studying membrane proteins is extremely difficult because of two basic reasons. First, membrane proteins are difficult to extract from cells, and purify after extraction. Second, even if extraction and purification are successful, the membrane proteins isolated from their native cellular membrane environment are often unstable and adapt conformations that are different from the actual native ones. Using viruses or bacterial cells, one can express membrane proteins using the machineries of the virus or bacteria on the surfaces. Binding kinetics of molecules with the membrane proteins can thus be studied with the present apparatus without the need of extracting the membrane proteins.

Studying Protein Conformational Changes

The functions of proteins are highly sensitive to the conformations of the proteins. Conformational changes in proteins may be caused by various factors, including temperature, solution pH, and interactions of the proteins with other species (ions, and molecules). A conformational change will change the movement of the protein in response to the applied voltage, and is, thus, detected with the present apparatus.

Identifying Proteins Based on the Mobility

Separating and identifying a protein based on its distinct mobility is widely used in protein analysis and purification. By analyzing the response of the proteins to the applied electric field in the present disclosure, one can determine the mobility and thus identify the proteins in a microarray format.

Identifying Proteins Based the Isoelectric Points

Another application is to identify proteins based on their characteristic isoelectric points. Although isoelectric point measurement can be performed by other platforms, the present technology can measure protein isoelectric points in the high throughput microarray format.

EXAMPLES

Detection of Different Types of Proteins

Figure 2A:
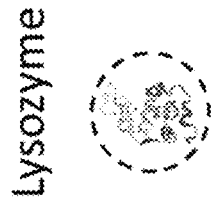
FIGS. 2A-2C show a plasmonic image of each of tethered proteins.
Figure 2A:
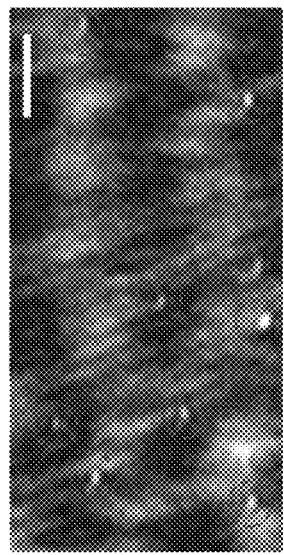
Figure 2B:
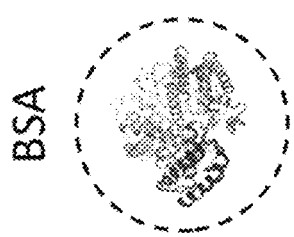
Figure 2B:
Figure 2C:
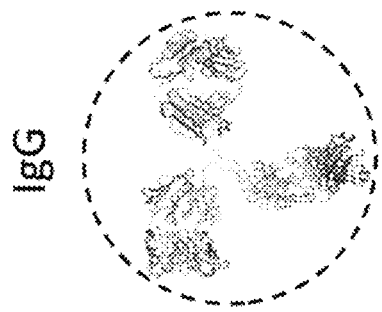
Figure 2C:

Referring to FIGS. 2A-C, proteins lysozyme, bovine serum albumin (BSA), and IgG are respectively tethered to a streptavidin coated ITO surface with a PEG linker (63 nm in length). The PEG contains a biotin group and a NHS group on either end respectively, where the biotin group conjugates streptavidin on the surface and the NHS group crosslinks with the proteins via NETS-amine reaction. An AC electric field (E ~800 V/m, f=80 Hz) is applied via a three electrode system to drive the proteins into oscillation. The buffer solution is 100 times diluted PBS. The images are recorded with a charge-coupled device (CCD) camera at 800 frames per second and the image contrast reflect the oscillation amplitude of proteins. Each image above shows fast Fourier transform (FFT) at 80 Hz over 1 second, where the red circles indicate single proteins. Scale bar=3 um.

While the preferred embodiments of the present technology have been illustrated in detail, it should be apparent that modifications and adaptations to those embodiments may occur to one skilled in the art without departing from the scope of the present technology.

What is claimed is:

1. An apparatus for analyzing and detecting interactions and reactions of proteins, comprising:
   an electrically conductive surface coated with streptavidin;
   a molecular bridge binding a protein to said surface, wherein the molecular bridge comprises polyethylene glycol having a number average molar mass of 1.6 kD to 160 kD and a biotin group and a N-hydroxysuccinimide group on either end of the polyethylene glycol, and wherein the biotin group conjugates the streptavidin on the surface;
   at least one electrode forming an alternating current (AC) electric field comprising a frequency between the at least one electrode and the surface and generating a response of the protein, wherein the response of the protein is periodic movement in response to the AC electric field;

a solution, wherein the surface, the molecular bridge, the protein, and at least a portion of the electrode are submerged in the solution and the electrode is disposed in the solution so that a direction of the electric field generated is substantially orthogonal to the surface;

a light emitting device exciting surface plasmons in the surface;

a sensor measuring a change in a distance between the protein and the surface; and a filter which detects the movement of the protein in the electric field thereby selectively detecting the response of the protein at the frequency.

2. The apparatus of claim 1, wherein the protein is directly bound to the molecular bridge.

3. The apparatus of claim 1, wherein the solution has a pH of about 5.3.

4. The apparatus of claim 1, wherein the surface comprises a glass substrate coated with a metal film.

5. The apparatus of claim 4, wherein the metal film has a thickness of about 47 nm and comprises gold.

6. The apparatus of claim 1, wherein the surface comprises a glass substrate coated with indium tin oxide.

7. The apparatus of claim 1, wherein the surface comprises a glass substrate coated with graphene.

8. The apparatus of claim 1, wherein the surface comprises a glass substrate coated with a thin carbon film.

9. The apparatus of claim 1, wherein the molecular bridge has a length from about 10 nm to about 999 nm.

10. The apparatus of claim 1, wherein a voltage of less than 10 volts is used to generate the electric field.

11. The apparatus of claim 1, wherein the frequency is from about 0.1 Hz to 10,000 Hz.

12. The apparatus of claim 1, further comprising a reference electrode.

13. The apparatus of claim 1, wherein the light emitting device is selected from the group consisting of a laser, a light emitting diode, and a superluminescent light emitting diode.

14. The apparatus of claim 1, wherein the sensor is selected from the group consisting of a surface plasmon resonance (SPR) sensor, a total internal reflection microscope, and a transmitted optical microscope.

15. The apparatus of claim 1, wherein the filter is a fast Fourier transform (FFT) filter.

16. The apparatus of claim 1, wherein the response is associated with a change in a charge of the protein.

17. An apparatus for analyzing and detecting interactions and reactions of proteins, comprising:

an electrically conductive surface coated with streptavidin;

a molecular bridge for binding a protein to the surface, wherein the molecular bridge comprises polyethylene glycol having a number average molar mass of 1.6 kD to 160 kD and a biotin group and a N-hydroxysuccinimide group on either end of the polyethylene glycol, and wherein the biotin group conjugates the streptavidin on the surface;

at least one electrode forming an electric field between the at least one electrode and the surface; and a solution, wherein the surface, the molecular bridge, and at least a portion of the electrode are submerged in the solution.

* * * * *